United States Patent

Hughes et al.

(10) Patent No.: US 8,057,545 B2
(45) Date of Patent: Nov. 15, 2011

(54) REVISION SPACER

(75) Inventors: Chris Hughes, Cordova, TN (US);
Randall Allard, Germantown, TN (US);
Robert Rice, Southaven, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1236 days.

(21) Appl. No.: 11/467,355

(22) Filed: Aug. 25, 2006

(65) Prior Publication Data

US 2008/0058939 A1 Mar. 6, 2008

(51) Int. Cl.
*A61F 2/44* (2006.01)
(52) U.S. Cl. .................................. 623/17.11
(58) Field of Classification Search ............... 606/246;
623/17.11–17.16
See application file for complete search history.

(56) References Cited

U.S. PATENT DOCUMENTS

| | | | |
|---|---|---|---|
| 5,314,477 A | 5/1994 | Marnay | |
| 5,507,816 A | 4/1996 | Bullivant | |
| 5,571,109 A | 11/1996 | Bertagnoli | |
| 5,888,226 A | 3/1999 | Rogozinski | |
| 6,375,681 B1 * | 4/2002 | Truscott | 623/17.11 |
| 6,740,118 B2 * | 5/2004 | Eisermann et al. | 623/17.14 |
| 6,758,862 B2 * | 7/2004 | Berry et al. | 623/17.16 |
| 6,776,798 B2 * | 8/2004 | Camino et al. | 623/17.16 |
| 6,899,734 B2 * | 5/2005 | Castro et al. | 623/17.16 |
| 7,235,101 B2 * | 6/2007 | Berry et al. | 623/17.11 |
| 7,255,714 B2 * | 8/2007 | Malek | 623/17.15 |
| 7,558,573 B2 * | 7/2009 | Stuempert et al. | 455/439 |
| 7,575,600 B2 * | 8/2009 | Zucherman et al. | 623/17.15 |
| 2004/0002759 A1 | 1/2004 | Ferree | |
| 2004/0030387 A1 * | 2/2004 | Landry et al. | 623/16.11 |
| 2004/0220670 A1 | 11/2004 | Eisermann et al. | |
| 2004/0230307 A1 | 11/2004 | Eisermann | |
| 2005/0060034 A1 * | 3/2005 | Berry et al. | 623/17.11 |
| 2005/0154459 A1 * | 7/2005 | Wolek et al. | 623/17.11 |
| 2007/0233261 A1 * | 10/2007 | Lopez et al. | 623/17.13 |

FOREIGN PATENT DOCUMENTS

| | | |
|---|---|---|
| FR | 2742653 A1 | 12/1995 |
| WO | 0042954 A2 | 7/2000 |
| WO | 0119295 A1 | 3/2001 |
| WO | 0101893 A1 | 11/2001 |
| WO | 0230337 A2 | 4/2002 |

* cited by examiner

*Primary Examiner* — Nicholas Woodall

(57) ABSTRACT

An intervertebral fusion device for promoting fusion of first and second vertebrae comprises first and second endplate modules. Each endplate module includes an outer surface adapted to interface with vertebral bone and an opposite inner surface. The endplate modules further include an attachment feature. A central module is adapted to extend between the first and second endplate modules and is further adapted for connection with the attachment feature. A through passage extends through the outer and inner surfaces of the each of the first and second endplates and through the central module.

24 Claims, 4 Drawing Sheets

REVISION SPACER

BACKGROUND

Spinal discs that extend between the endplates of adjacent vertebrae in a spinal column of the human body provide critical support between the adjacent vertebrae. These discs can rupture, degenerate and/or protrude by injury, degradation, disease or the like to such a degree that the intervertebral space between adjacent vertebrae collapses as the disc loses at least a part of its support function, which can cause impingement of the nerve roots and severe pain. In some cases, surgical correction may be required.

Typically, the surgical correction includes the removal of the spinal disc from between the adjacent vertebrae, and, in order to preserve the intervertebral disc space for proper spinal-column function, a prosthetic device is sometimes inserted in the intervertebral space between the adjacent vertebrae. In this context, the motion and alignment preserving prosthetic device may be referred to as an artificial disc, an intervertebral prosthetic joint or a prosthetic implant, among other labels.

In some cases, the inserted artificial disc may not function properly due to a wide variety of reasons such as, for example, failure of or damage to the artificial disc, poor tissue healing, the deterioration of the function and/or shape of the spinal column after the surgical correction, and/or other patient-related factors. In response, revision surgery, that is, another surgical correction, may be required in which the artificial disc is removed from the intervertebral space between the adjacent vertebrae. In other cases, the intervertebral space may be prepared to receive a prosthetic implant, when the surgeon determines that the patient would be better served by a fusion implant.

Thus, in either case, fusion of adjacent vertebrae previously prepared to receive a prosthetic joint may be the selected solution. Traditional fusion methods and devices may not provide the fit, stability, and/or alignment required to treat an intervertebral space prepared for a motion preserving device.

SUMMARY

In one embodiment, an intervertebral fusion device for promoting fusion of first and second vertebrae comprises first and second endplate modules. Each endplate module includes an outer surface adapted to interface with vertebral bone and an opposite inner surface. The endplate modules further include an attachment feature. A central module is adapted to extend between the first and second endplate modules and is further adapted for connection with the attachment feature. A through passage extends through the outer and inner surfaces of the each of the first and second endplates and through the central module.

In another embodiment, an intervertebral fusion device for promoting fusion of first and second vertebrae comprises an implant body, a first surface adapted to interface with the first vertebra, a second surface adapted to interface with the second vertebra, a keel extending from the first surface and adapted for insertion into the first vertebra, and an augmentation block adapted to interface with the first surface.

In still another embodiment, a method for promoting fusion of adjacent vertebrae comprises removing a first intervertebral implant from an intervertebral space between the adjacent vertebrae. The step of removing includes unseating a keel extension of the first intervertebral implant from a slot in at least one of the adjacent vertebrae. The method further includes selecting a second intervertebral implant. The second intervertebral implant includes first and second outer surfaces adapted to interface with the adjacent vertebrae. The method further includes inserting the second intervertebral implant into the intervertebral space between the adjacent vertebrae. The step of inserting includes positioning a keel extension of the second intervertebral implant into the slot in the at least one of the adjacent vertebrae. The method further includes depositing growth promoting material in a through passage extending from the first outer surface through the second outer surface.

Additional embodiments are included in the attached drawings and the description provided below.

DETAILED DESCRIPTION

Figure 1:
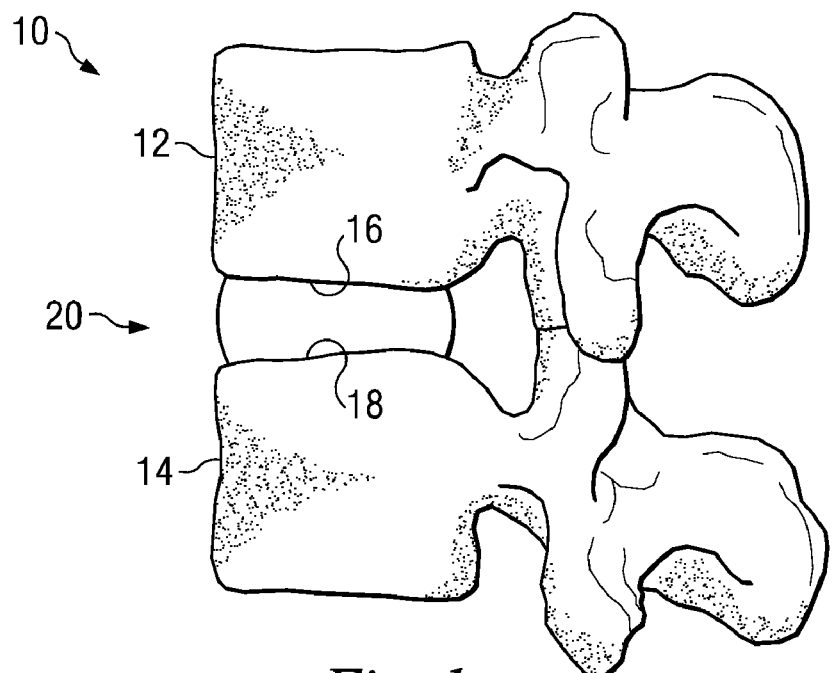
FIG. 1 is a sagittal view of a section of a vertebral column.

The present disclosure relates generally to devices and methods for fusing adjacent vertebral bodies and, more particularly, to devices and methods for fusing adjacent vertebral bodies prepared for receiving a motion preserving prosthetic implant. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral joint section or a motion segment of a vertebral column. The joint section 10 includes adjacent vertebral bodies 12, 14. The vertebral bodies 12, 14 include endplates 16, 18, respectively. An intervertebral disc space 20 is located between the endplates 16, 18.

Figure 2:
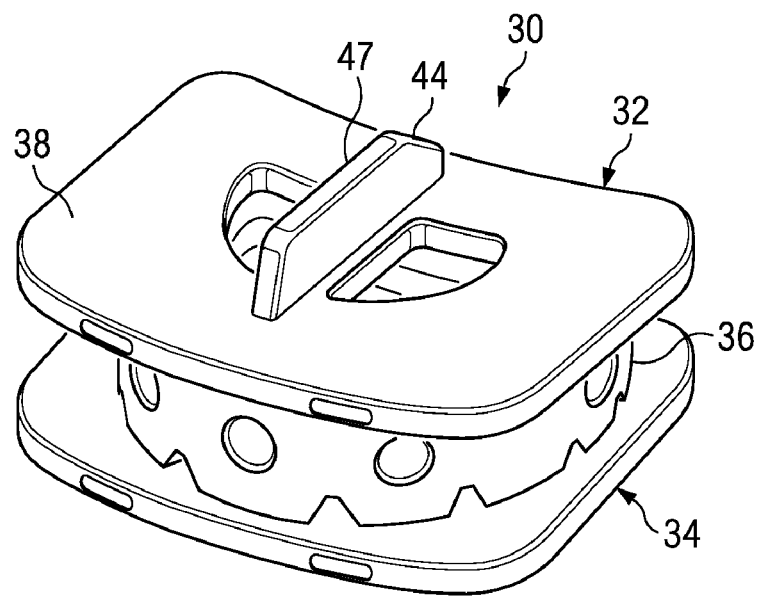
FIG. 2 is an assembled intervertebral fusion device according to one embodiment of the present disclosure.
Figure 3:
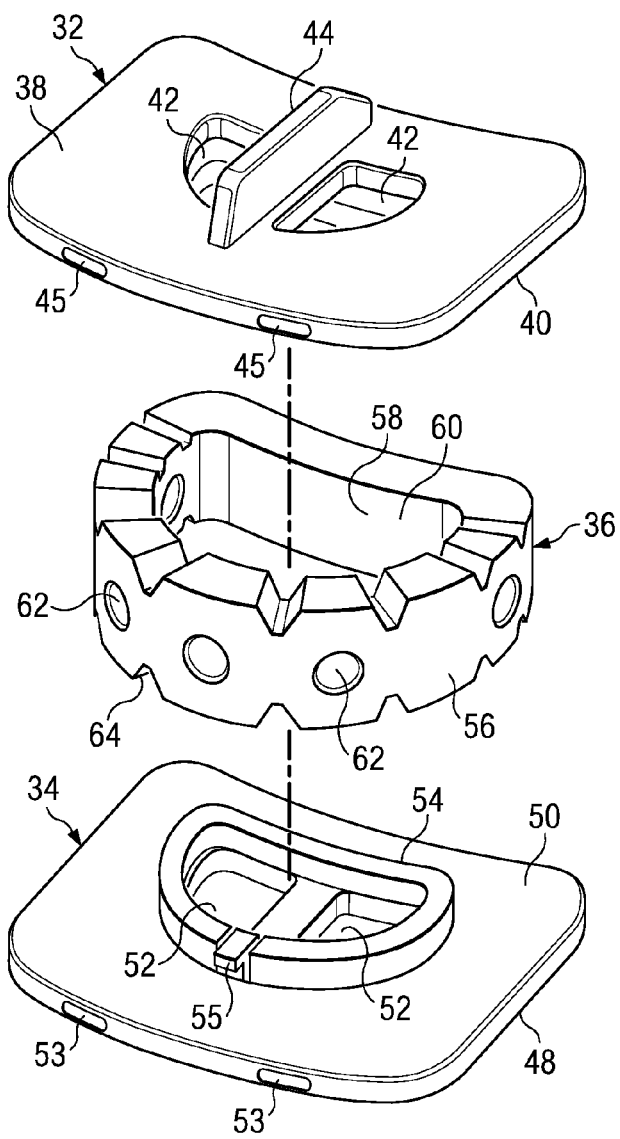
FIG. 3 is an exploded view of the intervertebral fusion device of FIG. 2.

Referring now to FIG. 2, in one embodiment an intervertebral fusion device is referred to by the reference numeral 30 and includes an upper endplate module 32, a lower endplate module 34, and a central module 36. The device 30 is modular in that the modules 32, 34, 36 may be selected separately to achieve a composite structure having a unique size, profile, or lordotic angle. The device 30 may be sized and shaped to occupy at least a portion of the intervertebral disc space 20.

The upper endplate module 32 includes an outer surface 38 and an inner surface 40 with passages 42 extending through the module 32 including through the outer and inner surfaces 38, 40. A keel 44 extends from the outer surface 38 and is adapted to engage the vertebral body 12 when the device 30 is inserted into the disc space 20. The upper endplate module 32 may further include access ports 45 to permit manipulation of the endplate module with an insertion or extraction tool. The ports 45 may also allow for eventual bone ingrowth. The upper endplate module 32 may also include one or more radiolucent markers 47 for monitoring the position of the device 30 during and after implantation using fluoroscopy.

The lower endplate module 34 includes an outer surface 48 and an inner surface 50 with passages 52 extending through the module 34 including through the outer and inner surfaces 48, 50. A keel (not shown) extends from the outer surface 48 and is adapted to engage the vertebral body 14 when the device 30 is inserted into the disc space 20. The lower endplate module 34 further includes a retaining wall 54 for maintaining the central module 36 in a fixed position and an attachment feature 55 for locking the central module 36 to the lower endplate module 34. A similar retaining wall (not shown) may be located on the inner surface 40 of the upper endplate module 32. The lower endplate module 34 may further include access ports 53 to permit manipulation of the endplate module with an insertion or extraction tool. The ports 53 may also allow for eventual bone ingrowth.

The central module 36 is, in this embodiment, generally D-shaped with an outer wall 56, an inner wall 58, and a through passage 60. The central module 36 includes access ports 62 to permit manipulation with an insertion or extraction tool. The access ports 62 may be through holes or closed at the inner wall 58. They may have threads or other fastening features for mating with the proper tool. The central module 36 may further include voids or notches 64 extending from the outer wall 56 through the inner wall 58 to allow for the positioning of bone graft and the eventual ingrowth of bone. The central module 36 may further include an attachment feature for securing the central module 36 to the lower endplate module 34.

The modules 32, 34, 36 may be at least partially composed of an osteogenic material, that is, a material that has the ability to promote, enhance and/or accelerate the growth of new bone tissue by one or more mechanisms such as, for example, osteogenesis, osteoconduction and/or osteoinduction. Examples of osteogenic materials include, but are not limited to, all types of bone and synthetic bone materials, including various types of allograft, autograft, allogenic and/or xenogenic materials, and/or any combination thereof. Polymers having a porous architecture such as porous polyetheretherketone (PEEK) may also be suitable. All or portions of the modules may be resorbable.

The surfaces of the modules 32, 34, 36, including the outer surfaces 38, 48, may include features or coatings which enhance the fixation of the implanted device. For example, the surfaces may be roughened such as by chemical etching, bead-blasting, sanding, grinding, serrating, and/or diamond-cutting. All or a portion of the surfaces may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include teeth, knurling, or other texturing to prevent migration of the device 30 and to promote bone ingrowth. In some instances, the outer surface of at least one of the endplate modules includes a titanium plasma spray.

As shown in FIG. 2, the intervertebral fusion device 30 may be assembled by positioning the central module 36 between the upper and lower endplate modules 32, 34. The assembly may be held together by locking the central module 36 to the lower endplate module 34 with the attachment feature 55. The central module 36 and the upper endplate module 32 may be similarly locked. The attachment feature 55 may have a releasable coupling interface with the central module 36 such as a snap fit wherein a portion of the attachment feature deforms to create a locking coupling.

Prior to implantation of the intervertebral fusion device 30, the disc space 20 may be prepared through discectomy to receive the device 30 or a motion preserving implant having a similar geometry such as the MAVERICK® artificial disc (distributed by Medtronic, Inc. of Minneapolis, Minn.) or in the form of an artificial disc embodiment described in detail in U.S. Pat. No. 6,740,118, the disclosure of which is incorporated by reference. As described in greater detail in U.S. patent application Ser. No. 10/768,354, which is incorporated by reference herein, the adjacent vertebral bodies 12, 14 may be prepared by forming slots adapted to receive keel extensions. With the disc space 20 prepared, the physician may determine whether a fusion implant or a motion preserving implant is suitable for the patient.

If the physician opts to fuse the adjacent vertebral bodies 12, 14, a fusion device such as device 30 may be inserted into the disc space 20 such that the keel 44 extends into the vertebral body 12 and the opposite keel extends into the vertebral body 14. The modularity of the device 30 allows the physician to select the modules 32, 34, 36 to create a composite device 30 having the height, lordotic angle, and/or material properties best suited to the patient.

If the physician chooses to preserve joint function the motion preserving implant may be installed. If, at a later time, further surgery is required to remove the motion preserving implant, conventional revision techniques may be used. Due to the removal of the motion preserving implant, contours generally corresponding to the implant may be defined in the endplates 16, 18, of the vertebrae 12 and 14, respectively. Furthermore, cavities may be formed in the endplates 16, 18 due to material loss from bone in-growth into the removed implant. That is, as the motion preserving implant is removed, bone or other natural material, connected to the implant due to in-growth, is also removed from the vertebrae, resulting in the formation of cavities. It is understood that, due to the removal of the motion preserving implant, additional bone and/or other material loss may occur in the vicinity of the vertebral bodies 12, 14, including other locations on the vertebral bodies.

The device 30 is inserted in the intervertebral space 20 between the vertebrae 12 and 14. At least a portion of the outer surface 38 engages the endplate 16, and at least a portion of the outer surface 48 engages the endplate 18. The keel 44 may be inserted into a cavity in the vertebral body 12 vacated by a keel of the motion preserving implant. The keel 44 may be wider and/or longer than the vacating keel to compensate for bone lost during the revision surgery. A similar revision device is implanted using a similar procedure as described in U.S. patent application Ser. No. 11/101,685 which is incorporated herein by reference.

Since the geometry of the device 30 generally corresponds to the geometry of the removed motion preserving implant, the engagement between the upper endplate module 32 of the device 30 and the vertebra 12 is facilitated, thereby minimizing the need for any material removal from the endplate 16 and/or other areas of the vertebra 12. Likewise, since the geometry of the device 30 generally corresponds to the geometry of the removed implant, the engagement between the lower endplate module 34 of the device 30 and the vertebra 14 is facilitated, thereby assisting to minimize the need for any material removal from the endplate 18 and/or other areas of the vertebra 14.

Before, during and/or after the insertion of the device 30 into the intervertebral space 20 between the vertebrae 12 and 14, filler material may be disposed in the opening formed by the through passages 42, 52, 60. The filler material may be composed of any type of material that has the ability to promote, enhance and/or accelerate the growth of new bone tissue by one or more mechanisms such as, for example, osteogenesis, osteoconduction and/or osteoinduction, including the types of materials identified above in connection with the device 30, or any combination thereof. Moreover, the filler material may be in the form of, for example, allograft chips, bone marrow, a calcium phosphate ceramic, a demineralized bone matrix putty or gel and/or any combination thereof. It is understood that the filler material may be injected into the passages 42, 52, 60 if the filler material is in the form of, for example, bone marrow, a bone matrix gel or a calcium phosphate cement which later hardens into a calcium phosphate ceramic within the passages. It is further understood that the filler material may be disposed in openings formed due to additional bone and/or other material loss in the vicinity of the vertebrae 12 and 14. Filler may be further be inserted into the access ports 45, 62, 53 and/or the voids 64.

After the insertion of the device 30 between the vertebral bodies 12, 14 has been completed, the device 30 may promote the fusion or joining together of the vertebral bodies 12, 14. During this fusion, the above-described structural and material properties of the device 30 allow and promote the growth of new bone material between the vertebral bodies 12, 14 so that the vertebral bodies 12, 14 biologically grow together and form a solid mass, thereby stabilizing the spine of which the vertebral bodies 12, 14 are a part. It is understood that bone in-growth may occur into any interconnected pores of the material of the device 30, from any natural source in the vicinity of the vertebral bodies 12, 14, including the vertebral bodies 12, 14.

Due to its above-described material properties, it is understood that the filler material in the passages 42, 60, 52 also promotes bone growth, serving as an adjunct to the fusion promotion of the device 30. It is further understood that the device 30 has sufficient rigidity and structural integrity to substantially maintain the height of the intervertebral space 20 between the vertebral bodies 12, 14, and to withstand any internal or external forces applied to the spinal column of which the vertebral bodies 12, 14 are a part.

Figure 4:
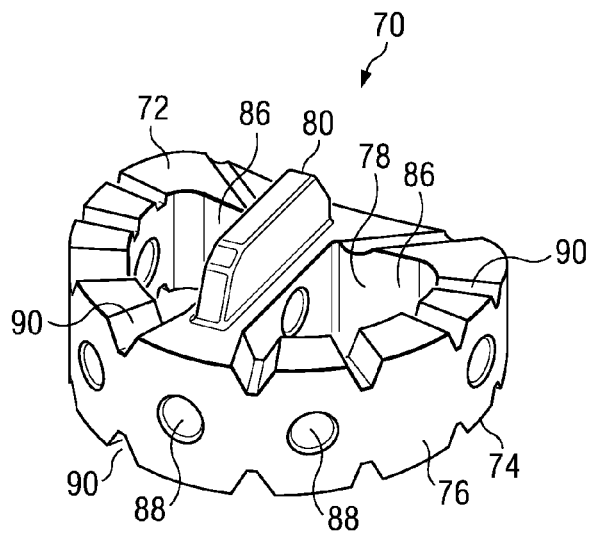
FIG. 4 is a perspective view of an intervertebral fusion device according to another embodiment of the present disclosure.
Figure 5:
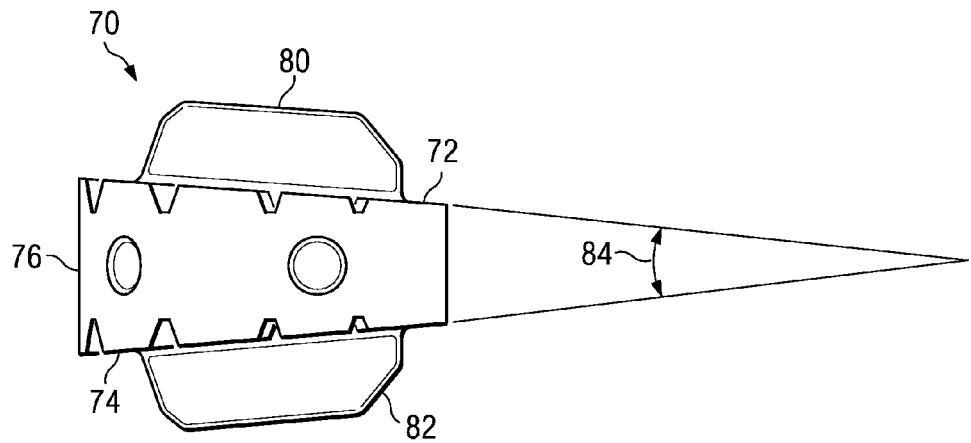
FIG. 5 is a side view of the intervertebral fusion device of FIG. 4.

Referring now to FIGS. 4 and 5, in another embodiment, an intervertebral fusion device 70 includes an upper surface 72, a lower surface 74, an outer surface 76, and an inner surface 78. An upper keel 80 projects from the upper surface 72 and a lower keel 82 projects from the lower surface 74. The device 70 may have a lordotic angle 84 defined between the upper surface 72 and the lower surface 74. Exemplary lordotic angles may be 6, 9, or 12 degrees.

The fusion device 70 may be a solid unitary or monolithic piece that is generally D-shaped to approximately match the geometry of the adjacent vertebral endplates 16, 18. Through passages 86 are defined through the device 70 and in communication with the upper and lower surfaces 72, 74. The device 70 includes access ports 88 to permit manipulation of the device with an insertion or extraction tool. The access ports 88 may be through holes or closed at the inner surface 78. They may have threads or other fastening features for mating with the proper tool. The access ports may be arranged about the device at, for example, 25 to 35 degree intervals. The device 70 may further include voids or notches 90 extending from the outer surface 76 through the inner surface 78 to allow for the positioning of bone graft and the eventual ingrowth of bone.

The fusion device 70 may be formed of any of the materials described above for modules 32, 34, 36. Likewise, all or selected ones of the surfaces 72, 74, 76, 78 or the keels 80, 82 may be coated or patterned to enhance the fixation of the implanted device using the materials or techniques described above for modules 32, 34, 36.

The monolithic device 70 may be installed substantially similar to the modular device 30 described above. Specifically, the device 70 may be selected to replace a keeled prosthetic implant such as the MAVERICK® artificial disc with the device 70 sized to accommodate not only the removed prosthetic implant, but also the vertebral endplate material lost during the revision surgery. The device 70 may be positioned within the disc space 20 such that the keels 80, 82 are arranged within the preformed slots in the vertebral bodies 12, 14, respectively, vacated by the keels of the prosthetic implant. The keels 80, 82 may be wider and longer than the keels of the prosthetic implant to compensate for bone lost during the revision surgery. It is understood that although the device 70 may be suitable to replace a prosthetic implant, it may also be used as an original implant into a newly prepared disc space.

As described above for device 30, filler material may disposed into the passages 88 to promote bone ingrowth and eventual fusion of the vertebral bodies 12, 14. The access ports 88 and the voids 90 may also receive filler material to aid in the fusion process. Filler materials such as those described above may be used with device 70.

Figure 6:
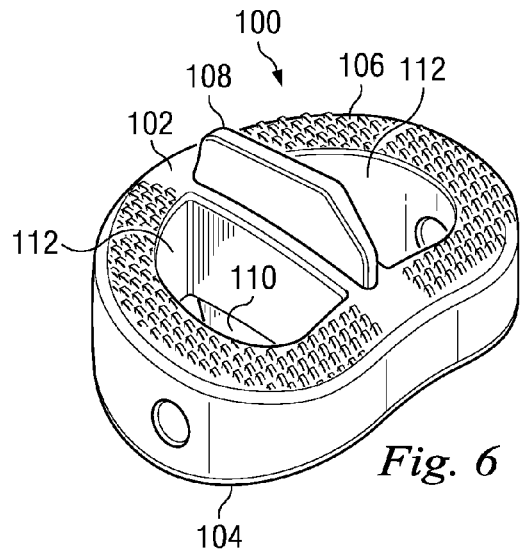
FIG. 6 is a perspective view of an intervertebral fusion device according to another embodiment of the present disclosure.
Figure 7:
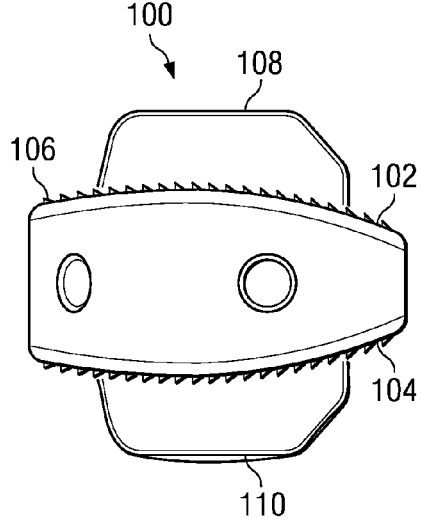
FIG. 7 is a side view of the intervertebral fusion device of FIG. 6.

Referring now to FIGS. 6 and 7, in still another embodiment, an intervertebral fusion device 100 may be configured substantially similar to the monolithic device 70 with the differences to be described. The device 100 may have upper and lower surfaces 102, 104, respectively, that are textured with a toothed pattern 106 that promotes bone ingrowth while providing friction-based stability to the implanted device 100 immediately after implantation. The device 100 further includes upper and lower keels, 108 and 110, respectively. The device 100 may further include through passages 112 extending through the device 100 and in communication with the upper and lower surfaces 102, 104. The toothed pattern 106 may accommodate a non-interfering machining pathway with the keels 108, 110.

Figure 8:
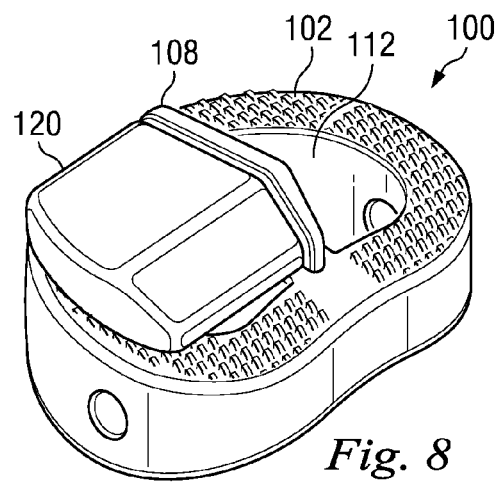
FIGS. 8-10 is a perspective view of the intervertebral fusion device of FIG. 6 with augmentation blocks.
Figure 9:
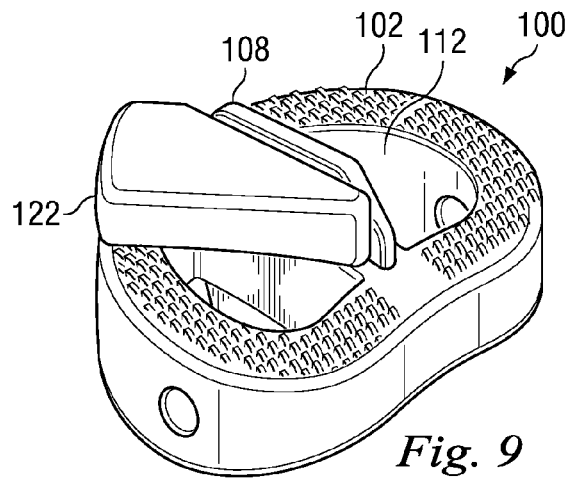
Figure 10:
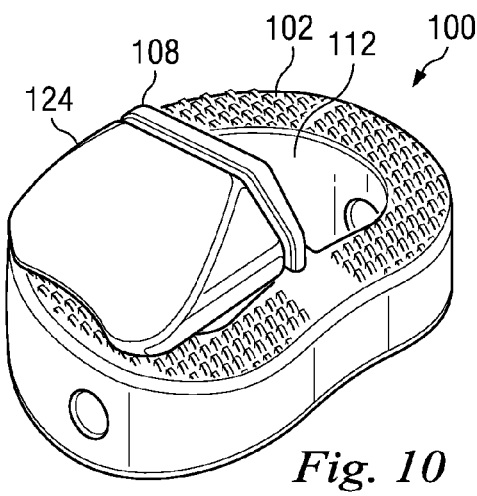

Referring now to FIGS. 8-10, augmentation blocks may be used to fill bone voids created during revision procedures that require resection of portions of the vertebral body to remove a prosthetic implant that has become overgrown and/or ingrown by bone. As shown in the embodiment of FIG. 8, an augmentation block 120 is sized and shaped to match the profile of the keel 108. The block 120 extends between the keel 108 and the upper surface 102 and may be particularly suited to bone lost in a direct lateral resection. The block 120 may have a locking fit such as a snap fit with the surface 102. For example, the block 120 may snap into the passage 112.

Referring now to the embodiment of FIG. 9, an augmentation block 122 is wedge shaped and sized for insertion adjacent to the keel 108. The augmentation block 122 may be particularly suited to augment the device 100 where the original prosthetic implant was removed with osteotomes using an anterior-oblique revision approach. In this embodiment the wedge-shaped augmentation block 122 tapers inward from an anterior edge of the device 100 toward a posterior edge of the device 100.

Referring now to the embodiment of FIG. 10, an augmentation block 124 is sized and shaped to match the profile of the keel 108 with a taper down from the keel toward the perimeter of the outer surface 102. The block 124 may be particularly suited for replacing bone resected using a direct lateral, but angled approach.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top" "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. An intervertebral fusion device for promoting fusion of first and second vertebrae, the device comprising:
   first and second endplate modules, each including an outer surface adapted to interface with vertebral bone, an opposite inner surface, a retaining wall extending from the inner surface, and an attachment feature, wherein a keel extends from a central portion of the outer surface;
   a central module adapted to extend between the first and second endplate modules and further adapted for connection with the attachment feature, the central module having an upper surface, a lower surface, an outer wall, and an inner wall, the inner wall defining an opening between the upper surface and the lower surface such that when the central module is positioned between the first and second endplate modules and connected with the attachment features of the first and second endplate modules the retaining walls of the first and second endplate modules are positioned within the opening of the central module to maintain the central module in a fixed position relative to the first and second endplate modules,
   wherein a pair of through passages extends through the outer and inner surfaces of the each of the first and second endplates such that the through passages are in communication with the opening of the central module when the central module is positioned between the first and second endplate modules and connected with the attachment features of the first and second endplate modules, wherein the pair of through passages are positioned on either side of the keel such that the keel separates the pair of through passages.

2. The intervertebral fusion device of claim 1 wherein the outer surfaces of the first and second endplate modules are planar.

3. The intervertebral fusion device of claim 1 wherein the attachment feature is a snap lock.

4. The intervertebral fusion device of claim 1 wherein the connection between the attachment feature and the central module is releasable.

5. The intervertebral fusion device of claim 1 wherein the central module comprises ports adapted to receive an insertion tool.

6. The intervertebral fusion device of claim 1 wherein the outer surface of at least one of the endplate modules is porous.

7. The intervertebral fusion device of claim 1 wherein the outer surface of at least one of the endplate modules includes a hydroxyapatite coating.

8. The intervertebral fusion device of claim 1 wherein the outer surface of at least one of the endplate modules includes a titanium plasma spray.

9. A prosthetic spinal device, comprising:
   a lower endplate module having an outer surface sized and shaped for engaging an lower vertebra, an inner surface opposite the outer surface, the inner surface including a protrusion and an attachment feature, at least two passages extending through the lower endplate module from the outer surface to the inner surface, and an engagement feature extending from the outer surface and positioned between the at least two passages;
   an upper endplate module having an outer surface sized and shaped for engaging an upper vertebra, an inner surface opposite the outer surface, at least two passages extending through the upper endplate module from the outer surface to the inner surface, and an engagement feature extending from the outer surface and positioned between the at least two passages; and
   a central module sized and shaped to be positioned between the upper and lower endplate modules, the central module having an upper surface for engaging with the inner surface of the upper endplate module, a lower surface for engaging with the inner surface of the lower endplate module, an outer wall, and an inner wall, the inner wall defining a single passage between the upper surface and the lower surface such that when the central module is positioned between the upper and lower endplate modules the protrusion of the lower endplate module the single passage of the central module to maintain the central module in a fixed position relative to the lower endplate module and such that the at least two passages of each of the upper and lower endplate modules are aligned with the single passage of the central module.

10. The prosthetic spinal device of claim 9, wherein the engagement feature is a keel.

11. The prosthetic spinal device of claim 10, wherein the protrusion of the lower endplate module surrounds the at least two passages of the lower endplate module.

12. The prosthetic spinal device of claim 11, wherein the protrusion has a D-shaped profile.

13. The prosthetic spinal device of claim 12, wherein the passage of the central module has a D-shaped profile.

14. The prosthetic spinal device of claim 13, wherein the attachment feature extends from a portion of the protrusion.

15. The prosthetic spinal device of claim 9, wherein the inner surface of the upper endplate module includes a protrusion and an attachment feature.

16. The prosthetic spinal device of claim 15, wherein the protrusions of the upper and lower endplate modules have a D-shaped profile that matches the profile of the passage of the central module.

17. The prosthetic spinal device of claim 16, wherein the first and second endplate modules have an outer profile shape that is different than an outer profile shape of the central module.

18. The prosthetic spinal device of claim 17, wherein the outer profile shape of the central module is D-shaped.

19. An intervertebral fusion device for promoting fusion of first and second vertebrae, the device comprising:
a first endplate module having:
- a body portion defining an outer surface configured for engagement with a vertebra, an opposing inner surface, and a pair of openings extending through the body portion from the outer surface to the inner surface;
- a D-shaped retaining wall extending from the inner surface, wherein the pair of openings are positioned within a boundary defined by the D-shaped retaining wall; and
- a bone-engaging protrusion extending from the outer surface and configured for engagement with the vertebra, the bone-engaging protrusion positioned between the pair of openings;

a second endplate module having:
- a body portion defining an outer surface configured for engagement with a vertebra, an opposing inner surface, and a pair of openings extending through the body portion from the outer surface to the inner surface;
- a D-shaped retaining wall extending from the inner surface, wherein the pair of openings are positioned within a boundary defined by the D-shaped retaining wall; and
- a bone-engaging protrusion extending from the outer surface and configured for engagement with the vertebra, the bone-engaging protrusion positioned between the pair of openings;

a central module sized and shaped to be positioned between and engaged with the first and second endplate modules, wherein the central module includes a single central passage extending between an upper surface and a lower surface such that when the central module is positioned between and engaged with the first and second endplate modules the pair of openings of each of the first and second endplate modules are in communication with the single central passage of the central module.

20. The intervertebral fusion device of claim 19, wherein the bone-engaging protrusion of the first endplate module is configured to slidingly engage the vertebra along an axis that is perpendicular to a longitudinal axis of the single central passage of the central module.

21. The intervertebral fusion device of claim 20, wherein each of the first and second endplate modules include attachment features for fixedly engaging with the central module to prevent separation of the first and second endplate modules from the central module along the longitudinal axis of the single central passage of the central module.

22. The intervertebral fusion device of claim 20, wherein the single central passage has a D-shape cross-sectional profile matching the D-shaped retaining walls of the first and second endplate modules.

23. The prosthetic spinal device of claim 19, wherein the first and second endplate modules have an outer profile shape that is different than an outer profile shape of the central module.

24. The prosthetic spinal device of claim 23, wherein the outer profile shape of the central module is D-shaped.

* * * * *